United States Patent
Herrmann

(10) Patent No.: US 7,027,148 B2
(45) Date of Patent: Apr. 11, 2006

(54) METHOD AND APPARATUS FOR DETERMINING THE TRIACETIN CONTENT IN FILTER PLUGS

(75) Inventor: Rainer Herrmann, Hamburg (DE)

(73) Assignee: TEWS Elektronik, Hamburg (DE)

( * ) Notice: Subject to any disclaimer, the term of this patent is extended or adjusted under 35 U.S.C. 154(b) by 574 days.

(21) Appl. No.: 10/136,107

(22) Filed: May 1, 2002

(65) Prior Publication Data
US 2003/0206023 A1 Nov. 6, 2003

(51) Int. Cl.
*G01N 21/00* (2006.01)
*G02B 27/32* (2006.01)
*A24C 5/18* (2006.01)
*G01R 27/04* (2006.01)
*G01R 27/32* (2006.01)

(52) U.S. Cl. .................. 356/256; 356/237.2; 131/84.1; 131/905; 131/906; 324/633

(58) Field of Classification Search ............. 356/237.2; 131/84.1, 905, 906
See application file for complete search history.

(56) References Cited

U.S. PATENT DOCUMENTS

| | | | | |
|---|---|---|---|---|
| 4,776,355 A | | 10/1988 | Stevenson et al. ........ | 131/352 |
| 4,848,370 A | * | 7/1989 | Federle et al. ............ | 131/84.1 |
| 5,060,664 A | * | 10/1991 | Siems et al. ............... | 131/84.1 |
| 5,736,864 A | * | 4/1998 | Moller ...................... | 324/633 |

FOREIGN PATENT DOCUMENTS

| | | |
|---|---|---|
| DE | 28 15 025 A1 | 10/1979 |
| EP | 0 889 321 A1 | 1/1999 |
| EP | 0 908 718 A1 | 4/1999 |
| WO | WO 91/12518 | 8/1991 |

OTHER PUBLICATIONS

E. Samios, et al., "Preparation, characterization and biodegradation studies on cellulose acetates with varying degrees of substitution", Polymer vol. 38 No. 12, pp. 3045-3054, 1997, G.B., Elsevier Science Ltd., Publishers.

* cited by examiner

Primary Examiner—Hwa (Andrew) Lee
Assistant Examiner—Gordon J. Stock, Jr.
(74) Attorney, Agent, or Firm—Alix, Yale & Ristas, LLP

(57) ABSTRACT

Apparatus and method for determining the triacetin content in cigarette filter plugs during the manufacture of the filter plugs from a filter tow. The apparatus including a filter tow storage container, a filter tow stretching device, a device for feeding triacetin, to the filter tow, a plug-forming device, a device for dividing the plug into portions, a first microwave sensor disposed downstream of the plug-forming device, and a second microwave sensor disposed upstream of the feed device for the triacetin. The triacetin content is determined by transmitting a high frequency electromagnetic field through the filter plug both before and after the triacetin is added and measuring the frequency shift and spread of the electromagnetic field to determine mass signals $A_t$ and $A_0$, respectivley. $A_0$ is compared to $A_t$ to calculate the triacetin content of the filter plug.

13 Claims, 3 Drawing Sheets

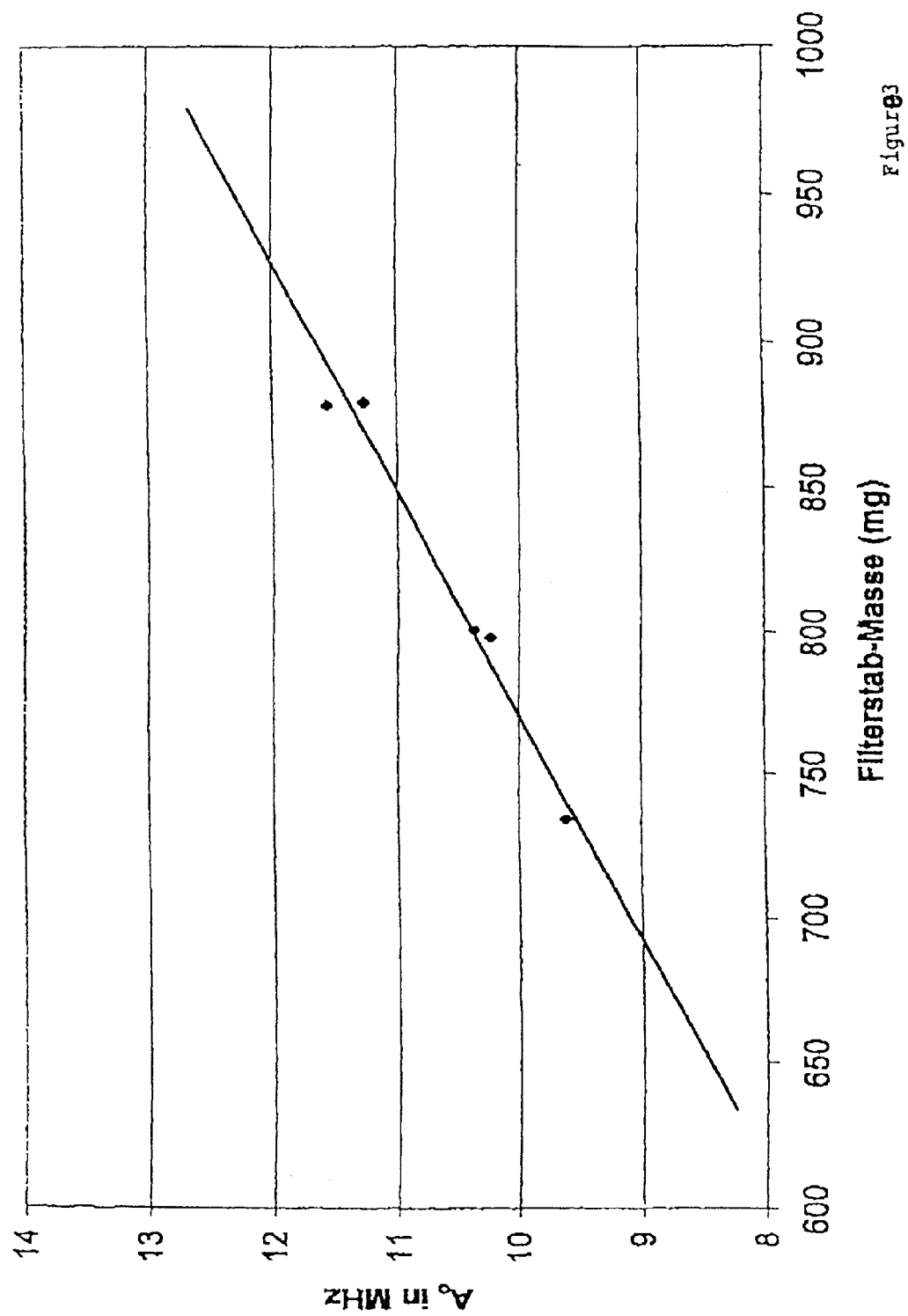

METHOD AND APPARATUS FOR DETERMINING THE TRIACETIN CONTENT IN FILTER PLUGS

BACKGROUND OF THE INVENTION

The invention relates to a method and an apparatus for determining the triacetin content in filter plugs for cigarettes during the manufacture of the filter plugs from a filter tow consisting of, in particular, cellulose acetate.

Cigarette filters generally consist of cellulose acetate and contain triacetin, specifically typically in an amount of approximately 8% (m/m). The triacetin is essential for the filter action.

Currently there is no reliable possibility whatsoever for determining or even controlling the triacetin content online during filter manufacture. Therefore filter manufacturers in general resort to a laboratory method by taking filter samples with and without triacetin from the process and comparing these offline by weighing. The consequence is that in the event of the supply of triacetin stopping suddenly (for example when a container is empty, a solenoid valve becomes stuck, etc.) this is usually noticed only at the time of the next offline laboratory check. However, if a filter plug is produced without an adequate supply of triacetin, the filter action deteriorates to such an extent that the health-promoting measures of the filter are non-existent. If the damage is not noticed in good time, many millions of cigarettes which have already been produced, and frequently have already been packed, have to be broken up again and returned to production. After the tobacco, the filter material is the most expensive starting material. The filter material cannot be recycled. Considerable costs are thus incurred.

Previous attempts using other physical methods to determine the filter mass and to control the supply of triacetin have not led to success.

For instance, it is known to determine the filter mass on the plug with the aid of a radioactive beta radiation emitter and detector (DE 28 IS 025 A). However, because the degree of interaction between the lightweight mass of the filter plug and the beta radiation is too low and because of the restriction of detecting only a damping signal of the electrons, in the case of simultaneous fluctuations in the moisture content, filter tow content and triacetin content the accuracy of measurement with this method is too low to achieve a reasonable weight or triacetin control. A method developed in the 1990s for the use of infra-red absorption lines of the triacetin for triacetin determination did not result in adequate accuracies because the near infra-red absorption method, as an optical measurement procedure is only a surface measurement method and is able to penetrate only a few wavelengths, that is to say a few micrometers, into the product. Measurement of the triacetin content downstream of the cutter downstream of the filter maker and vertically to the cut edge of the filters was also not able to compensate for this fundamental defect of the IR method (instrument from cooperation between Moisture Systems, Hopkinton and Celanese, Charlotte, USA). At the same time, only a minute portion of the product is detected within the NIR measurement radiation and within the penetration depth by this means.

SUMMARY OF THE INVENTION

The aim of the invention is to provide a reliable and sensitive method and a corresponding apparatus for determining the triacetin content in filter plugs during the manufacture of these filter plugs.

The solution according to the invention consists in that the shift and spread of the resonance curve of a resonator through filter material is determined using high frequency measurement methods before and after addition of triacetin and the triacetin content is determined from this. Here "high frequency" is understood to be not only radio frequency but also hyperfrequency and microwave frequencies.

The measurement is thus not carried out with beta rays, which have only a relatively low degree of interaction with the material and in addition could have in adverse advertising effect since the consumer could be scared off because of only inaccurate ideas about the effect of radioactive radiation. On the contrary, high frequency is used, which has a substantially greater interaction with the filter material and triacetin contained therein than does beta radiation. On the other hand, the high frequency also penetrates through the entire material, so that it is not only a surface region that is detected, as is the case with the infra-red measurements that have been mentioned.

The determination of mass and moisture content of materials with the aid of high frequency, in particular microwaves, is known (EP 0 468 023 B1, EP 0 889 321 A1, EP 0 908 718 A1). However, these known methods and equipment, in the name of the Applicant, are only examples. Of course, mass and moisture content can also be determined with modified methods, by, for example, determining the resonance curves or selected points on these resonance curves in other ways in order to obtain the result. The equipment can, of course, take a different form to that described in the cited prior art. Quite generally, arbitrary high frequency measurement methods with which ma, and moisture content can be determined can be used.

According to the invention it has now been found that not only the moisture content (water content), as in the state of the art, but also the triacetin content can be determined. It is true that identical quantities of water and triacetin have a different effect on the shift of the resonance frequency and the spread of the resonance curve. Nevertheless, surprisingly, the triacetin content can, however, also be determined by this shift and spread of the resonance curve with the aid of corresponding calibration measurements. For this purpose the effect of the filter plug provided with triacetin, on the shift and spread of the resonance curve is determined and the triacetin content is then calibrated by laboratory measurement. With this procedure a linear relationship with the triacetin content is obtained, for example, for the shift of the resonance frequency and specifically essentially independently of the specific machine (filter maker) on which the filter plug is produced, independently of specially selected filter tow material, independently of the method by which triacetin is supplied, independently of the plug speed at which the filter plug is produced and also independently of the original moisture content of the material and of the final moisture content. This is essential, since at a lower plug speed a lower final moisture content is obtained as a result of drying out during production in the machine.

A microwave resonator that is so constructed that a sufficiently large interaction exists between the microwave field in the resonator and the filter plug (EP 0 889 321 A1) is subjected by the filter plug material to resonance frequency detuning that at increases with increasing triacetin content, but also with increasing filter tow mass and with increasing moisture content. With this resonator, the triacetin content can be determined by determining the resonance frequency detuning of filter plug provided with triacetin compared with a filter plug that is not provided with triacetin.

A particularly appropriate method of the invention that requires only one microwave sensor is characterized in that the measurements on the finished filter plug are carried out first without the addition of triacetin and then with the addition of triacetin. With this method the difference in the measured values, in particular the resonance shifts, gives the triacetin content. Thus, the filter production can first of all be carried out without triacetin, for, for example, ten seconds and the resonance shift determined. The resonance shift is then determined continuously while triacetin is added. The difference value then gives the triacetin content. Since the mass of the filter material or the original moisture content of the latter could change over time, an incorrect triacetin value could be obtained. In order to prevent this, a reference measurement without the addition of triacetin will again be carried out after a certain period of, for example 30 minutes, in order to take account of changes that have occurred in the interim.

In another advantageous embodiment, mass and moisture content of the filter tow material supplied are determined by a second sensor at a point at which no triacetin has yet been added. On the basis of the known geometry and the ratio of the speeds at which the filter tow enters the machine and the filter plug emerges from the latter, the mass or density of the filter plug which the latter possesses without the addition of triacetin can then be determined. With this arrangement the abovementioned reference measurement on the finished plug can then be dispensed with and it is then necessary only to carry out the measurement with added triacetin at this point. This method has the advantage that the addition of triacetin does not have to be interrupted at the start or even from time to time.

However, it is particularly advantageous if measurements on the filter material without added triacetin are carried out at both measurement points, upstream and downstream of the feed point for triacetin. In this way the two measurement methods are combined. With this method a correction in the value for the mass of the finished plug without triacetin can be carried out between two calibrations, in which a filter plug without triacetin is produced, by determining changes in the initial density or initial moisture content of the filter tow. Thus, for example, it could be established that when the moisture content at the input increases by 3% the moisture content at the output also increases by 3% or perhaps also increases by a smaller value of only 2.5%. These are all parameters that can be found empirically and can be taken into account when correcting the basic value for the filter plug without triacetin.

Advantageously, the measurements are carried out using a high frequency of 10 MHZ to 30 GHz. Frequencies between 100 MHZ and 20 GHz or between 500 MHZ and 15 GHz are even more advantageous. Microwaves are very particularly advantageous, in particular also because of the size of the filter plugs [lacuna] measured.

In a preferred embodiment the results of the measurements can be used to control the triacetin addition. By this means it is possible, on the one hand, to prevent the triacetin content being too low, whilst, on the other hand, too high a triacetin content, which gives rise to unnecessary costs, can also be avoided.

Advantageously, a warning is given and/or the equipment is switched off if the amount of triacetin is below a minimum amount or above a maximum amount.

An apparatus for carrying out the method is characterized in that it has a storage container for the filter tow, a stretching device for the filter tow, a feed device for the triacetin, a plug-forming device and a device for dividing the plug into portions, wherein, according to the invention, a microwave sensor is provided downstream of the plug-forming device. In a further advantageous embodiment a further microwave sensor is provided upstream of the feed device for the triacetin.

BRIEF DESCRIPTION OF THE DRAWINGS

The invention will be described below by way of example on the basis of an advantageous embodiment with reference to the appended drawings. In the drawings:

FIG. 3 shows the dependency of the resonance frequency shift on the mass of the filter.

DETAILED DESCRIPTION OF THE PREFERRED EMBODIMENT

Figure 1:
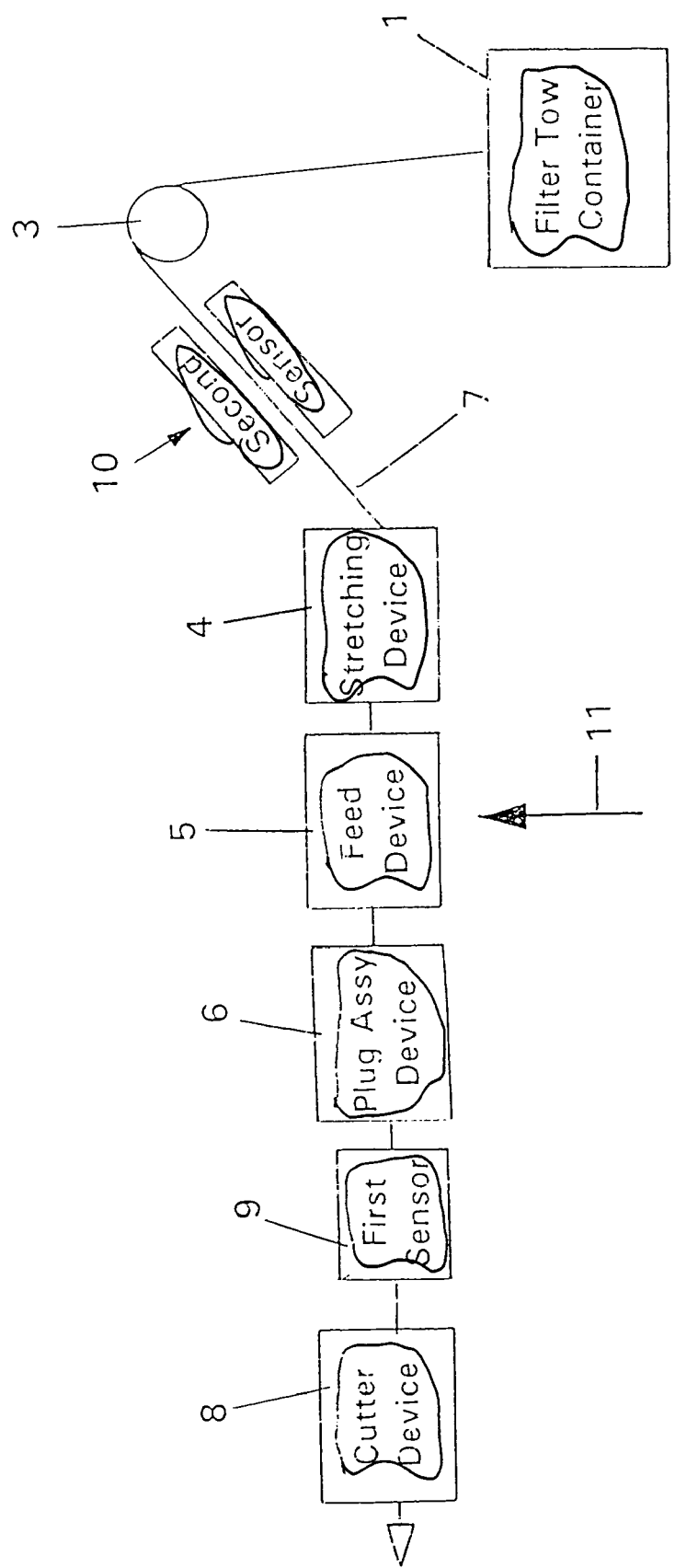
FIG. 1 shows the principle of a circuit for an apparatus for the production of the filter plug (filter maker)

The principle of a machine for the production of a filter plug (filter maker) is shown in FIG. 1. The filter tow is a tape of cellulose acetate that is placed in a filter tow container 1 and is taken from the latter in the form of this taps 2. A transport device and deflecting device for the filter tow 2 are shown diagrammatically at 3. A stretching device for the filter tow, in which this tow is spread for the subsequent addition of triacetin, is indicated by 4. 5 is a feed device into which the triacetin is fed, as is indicated by the arrow 11. Plug formation, wrapping in paper and sticking the paper take place in the equipment 6. The finished filter plug 7 provided with triacetin obtained in this way is then subdivided into pieces of equal length by a cutter device at 8, which pieces are then fed to the machines for the production of the filter cigarettes.

A first microwave sensor by means of which the mass and moisture content and also the triacetin content of the finished filter plug 7 can be determined is at 9. As has been mentioned, with this procedure the mass and moisture content without triacetin can be determined first of all and subsequently the mass and moisture content with triacetin can be determined in order thus to determine the triacetin content. A second microwave sensor by means of which the mass and moisture content of the original filter tow tape can be determined is shown at 10.

Figure 2:
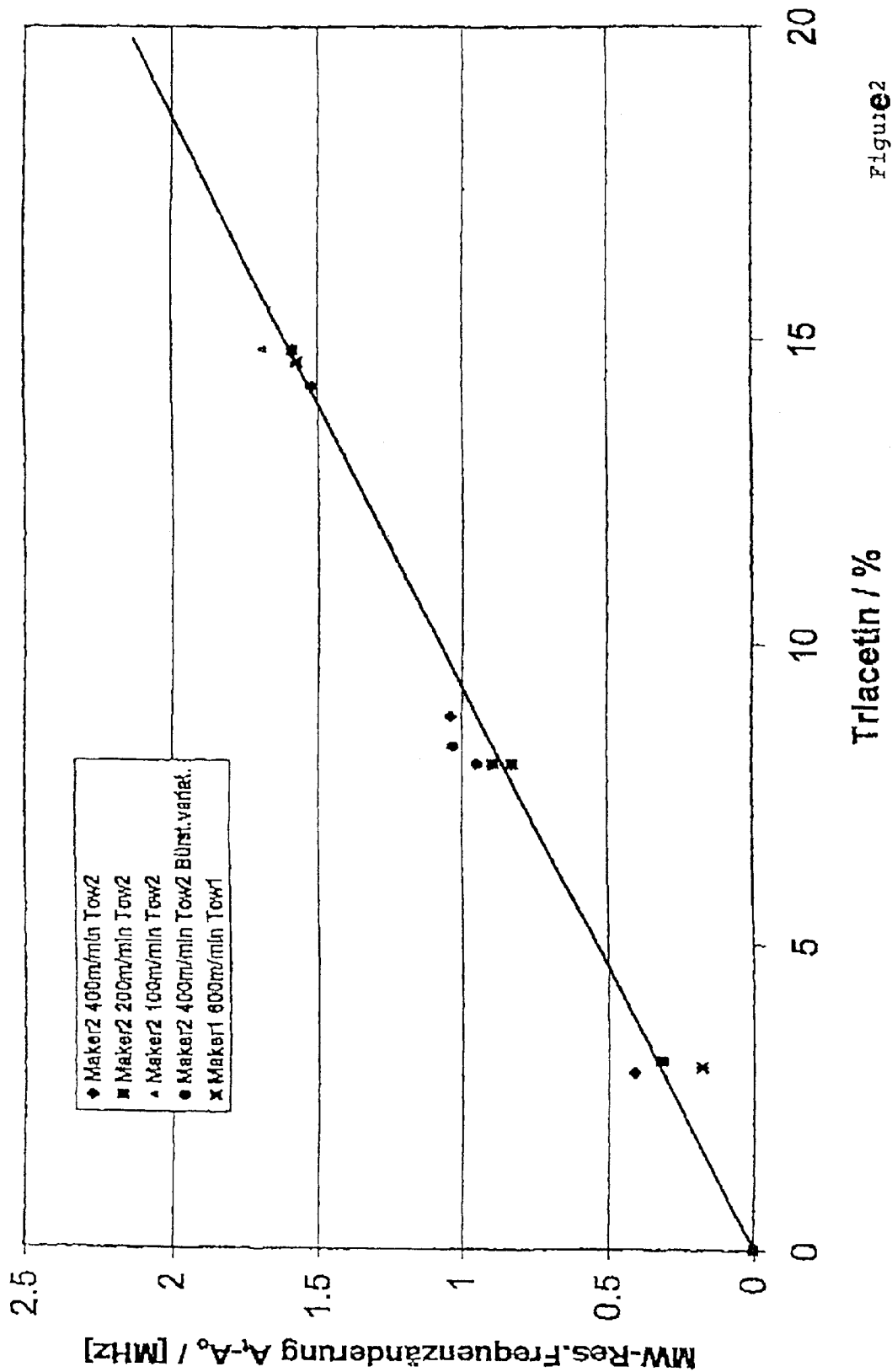
FIG. 2 shows a typical resonance frequency shift as a function of the triacetin content for various conditions.

FIG. 2 shows the difference in density value compared with the state without the addition of triacetin, as a function of the triacetin concentration for various machines and production methods. The linear relationship irrespective of the particular machine or the production parameters is clearly discernible. In this figure the difference in density value is indicated in MHZ, that is to say the shift in the resonance frequency.

FIG. 3 shows the frequency shift in the resonance frequency for a filter, which is produced at the output by subdividing the filter plug, without triacetin as a function of its mass.

With the aid of a microwave apparatus for determining moisture content and density from the abovementioned state of the art, it is possible with the aid of a sensor suitable for measurement of the filter plug to compare the mass signal [lacuna] (frequency shift) $A_t$ with the mass signal of the filter plug without triacetin $A_0$. For this purpose the sensor must be installed in the filter plug machine at the output just upstream of the cutter position, where plug formation has been completed. The difference in value between the two mass signals $A_t$–$A_0$ is calibrated against the amount of triacetin, which can be effected by laboratory determinations of the weight. This difference parameter is largely insensitive to charges in the operating conditions of the machine, the production rate, the amount of filter tow material used, the way in which the triacetin is applied, etc. The reference parameter $A_0$ contains all information on the nature of the filter without triacetin and can be determined at the start of a new production cycle if a filter plug is initially produced without triacetin for a short period. The moisture content value $F_0$ without interference by the triacetin can also be determined at the same time. In order to detect changes in the reference parameter, this procedure can be repeated at intervals.

If only this type of pure difference measurement is to be carried out, an absolute determination of the mass or density of the filter plug is not required in every measurement. This mass can, however, also be determined absolutely if a measurement without filter plug is carried out first of all and mass and moisture content are then determined absolutely from the shift in the resonance frequency and spread of the resonance curve.

In an advantageous embodiment the second microwave sensor 10 for the filter tow tape 2 is also provided, which sensor is preferably a planar sensor or fork resonator. Here it is possible to determine mass and moisture content of the filter tow tape 2. If these values change during the production of the filter plug, cost-correction of the value $A_0$ Of the microwave sensor 9 can be carried out, as a result of which a greater accuracy is obtained. For this purpose the amount M and the moisture content F of the fiber material, that passes into the machine, are determined simultaneously at the input to the machine by the sensor 10. The mass $M_0$ of the dry input fibre material can be determined from these values. The two measurement parameters $M_0$ and F can serve as the basis for the determination of the reference parameter $A_0$ of the microwave sensor 9 at the output of the filter machine, since in the case of known values for the compaction of the fibre material (that is to say the ratio of the speeds of the plug at the input and at the output as known machine data) $A_0$ is an unambiguous function of $M_0$ and F that can be calibrated.

What is claimed is:

1. A method for determining the triacetin content in cigarette filter plugs during the manufacture of the filter plugs from a filter tow comprising cellulose acetate, the method comprising the steps of:
   (a) transmitting a high frequency electromagnetic field through the filter plug prior to the addition of the triacetin to the filter plug;
   (b) measuring the frequency shift and spread of the electromagnetic field to determine a mass signal $A_t$;
   (c) transmitting a high frequency electromagnetic field through the filter plug after the addition of the triacetin to the filter plug;
   (d) measuring the frequency shift and spread of the electromagnetic field to determine a mass signal $A_0$; and
   (e) comparing $A_0$ to $A_t$ to calculate the triacetin content of the filter plug.

2. The method of claim 1, further comprising repeating steps (a) and (b) after a specified period.

3. The method of claim 1, wherein steps (a) and (b) are carried out upstream of the feed point for triacetin.

4. The method of claim 2, wherein steps (a) and (b) are first carried out at a first measurement point upstream of the feed point for triacetin and subsequently at a second measurement point upstream of the feed point for triacetin.

5. The method of claim 3, during steps (a) and (b), the mass and the moisture content of the filter tow are determined.

6. The method of claim 1, wherein the electromagnetic field has a frequency of 10 MHZ to 30 GHz.

7. The method of claim 1, wherein the electromagnetic field has a frequency of 100 MHZ to 20 GHz.

8. The method of claim 1, wherein the electromagnetic field has a frequency of 500 MHZ to 15 GHz.

9. The method of claim 1, wherein the electromagnetic field comprises microwaves.

10. The method of claim 1, further comprising the step of controlling the triacetin addition on the basis of the calculated triacetin content.

11. The method of claim 1, further comprising the step of giving a warning if the calculated amount of triacetin is below a minimum amount or above a maximum amount.

12. The method of claim 1, further comprising the step of stopping manufacture of the filter plugs if the calculated amount of triacetin is below a minimum amount or above a maximum amount.

13. An apparatus for manufacturing a cigarette filter plug from a filter tow comprising:
   a storage container storing for the filter tow,
   a stretching device for stretching the filter tow,
   a feed device for feeding triacetin,
   a plug-forming device,
   a portioning device for dividing the plug into portions,
   a first microwave resonator disposed downstream of the plug-forming device, and
   a second microwave resonator disposed upstream of the feed device for the triacetin.

* * * * *